US006518419B1

(12) United States Patent
Van Der Lugt et al.

(10) Patent No.: US 6,518,419 B1
(45) Date of Patent: Feb. 11, 2003

(54) PROCESS FOR SELECTIVE OXIDATION OF PRIMARY ALCOHOLS

(75) Inventors: Jan Pieter Van Der Lugt, Amersfoort (NL); Jan Matthijs Jetten, Zeist (NL); Arie Cornelis Besemer, Amerongen (NL); Hendrik Arend Van Doren, Amersfoort (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 120 days.

(21) Appl. No.: 09/706,767

(22) Filed: Nov. 7, 2000

Related U.S. Application Data

(63) Continuation-in-part of application No. PCT/NL99/00272, filed on May 4, 1999.

(30) Foreign Application Priority Data

May 7, 1998 (EP) .............................................. 98201495

(51) Int. Cl.[7] .......................... C08B 31/18; C07H 1/00; C07G 17/00; C07C 45/00
(52) U.S. Cl. .................... 536/105; 536/123.1; 536/124; 554/13; 562/419; 562/565; 568/432; 568/436; 568/437; 568/484
(58) Field of Search .............................. 536/105, 123.1, 536/124; 554/13; 562/419, 515; 569/432, 436, 437; 568/484

(56) References Cited

U.S. PATENT DOCUMENTS 5,334,756 A  8/1994  Likibi et al.
5,362,868 A  11/1994  Eul et al.
5,739,352 A  4/1998  Barner et al.

OTHER PUBLICATIONS

Nooy et al. "Highly selective nitroxyl radical–mediated oxidation of primary alcohol groups in water–soluble glucans". Carbohydrate Research 269.(1995) pp. 89–98.*

Chang et al. "Oxidation of the primary alcohol groups of cyclomaltodextrins with 2,2,6,6–tetramethyl–1–piperidine oxoammonium ion". Carbohydrate Letters. vol. 3 (1997) pp. 31–38.*

Jacques Einhorn et al., "Efficient and Highly Selective Oxidation of Primary Alcohols to Aldehydes by N–Chloro-succinimide Mediated by Oxoammonium Salts," J. Org. Chem., 1996, vol. 61, pp. 7452–7454.

A.E.J. de Nooy et al., "Highly Selective Tempo Mediated Oxidation of Primary Alcohol Groups in Polysaccharides," Receuil des Travaux Chimiques des Pays–Bas, vol. 113, Mar. 3, 1994, pp. 165–166.

* cited by examiner

Primary Examiner—Johann Richter
Assistant Examiner—Sikarl A. Witherspoon
(74) Attorney, Agent, or Firm—Young & Thompson

(57) ABSTRACT

Primary alcohols, especially in carbohydrates, can be selectively oxidized to aldehydes and carboxylic acids in a low-halogen process by using a peracid in the presence of a catalytic amount of a di-tertiary-alkyl nitroxyl (TEMPO) and a catalytic amount of halide. The halide is preferably bromide and the process can be carried out at nearly neutral to moderately alkaline pH (5–11). The peracid can be produced or regenerated by means of hydrogen peroxide or oxygen. The process is advantageous for producing uronic acids and for introducing aldehyde groups which are suitable for crosslinking and derivatization.

12 Claims, No Drawings

PROCESS FOR SELECTIVE OXIDATION OF PRIMARY ALCOHOLS

This application is a continuation-in-part of international application PCT/NL99/00272 filed May 4, 1999, which designated the United States.

The invention relates to the selective oxidation of primary alcohols, using an oxidizing agent in the presence of a catalytic amount of a di-tertiary-alkyl nitroxyl compound, especially 2,2,6,6-tetramethylpiperidin-1-oxyl (TEMPO).

Such a process is known from *Tetrahedon Lett.* 34, 1181–1184 (1993), which describes the oxidation of monosaccharides wherein the non-primary hydroxyl groups are partly protected, using sodium hypochlorite, potassium bromide and TEMPO in a two-phase solvent system (dichloromethane and water) to produce the corresponding uronic acid. WO 95/07303 describes a process for oxidizing carbohydrates with hypochlorite/TEMPO, using a pH of 9–13 in an aqueous medium. The oxidation of carboxymethyl and hydroxyethyl derivatives of starch and cellulose and other starch ethers with TEMPO is described in WO 96/38484.

These prior art oxidations have the advantage of being selective, in that oxidation of primary alcohol groups is strongly favored over oxidation of secondary alcohol groups. However, the known processes use hypochlorite as the actual oxidizing agent and thus produce chloride and some chlorinated byproducts: for complete oxidation of primary alcohols to carboxylic acids, two molar equivalents of hypochlorite are used and two molar equivalents of chloride are produced. This is serious drawback as there is an increasing need for low-chlorine or even chlorine-free oxidation processes.

It was found now that the oxidation of primary alcohol functions can be carried out without using equivalent amounts of chlorine compounds and with the possibility of using hydrogen peroxide as the ultimate oxidizing agent. The process of the invention is defined by the characterizing features of the appending claims.

In the following description, reference is made to TEMPO only for the sake of simplicity, but it should be understood that other di-tert-alkyl nitroxyls, such as 4,4-dimethyloxazolidine-N-oxyl (DOXYL), 2,2,5,5-tetramethylpyrrolidine-N-oxyl (PROXYL) and 4-hydroxy-TEMPO and derivatives thereof and those described in WO 95/07303 can be substituted for TEMPO. The catalytic amount of nitroxyl is preferably 0.1–2.5% by weight, based on the primary alcohol, or 0.1–2.5 mol % with respect to the primary alcohol.

The halide present in the process of the invention serves for regenerating TEMPO. The halide may be chloride, but preferably it is bromide. The halide may be added to the reaction mixture as such, but it may also be added as an equivalent thereof or as molecular halogen. The halide ions are oxidized to molecular halogen by the peracid, and the molecular halogen regenerates TEMPO. Thus, both TEMPO and the halide need to be present in a catalytic amount only. The catalytic amount of halide may be 0.1–40, preferably from 0.5 to 10 mol %, with respect to the primary alcohol.

The peracid may be any peralkanoic acid such as peracetic acid, perpropionic acid, perlauric acid etc., a substituted alkanoic acid such as peroxytrifluoroacetic acid, an optionally substituted aromatic peracid such as perbenzoic acid or m-chloroperbenzoic acid, or an inorganic peracid such as persulfuric acid. The peracids may be formed in situ from a precursor such as the corresponding aldehyde, (carboxylic) acid, acid anhydride, ester or amide, e.g. tetra-acetyl-ethylenediamine, with a suitable halogen-free oxidizing agent, such as hydrogen peroxide or oxygen, either before the oxidation reaction or during the oxidation reaction.

The process of the invention results in oxidation of primary alcohols initially to the corresponding aldehydes, and eventually to the corresponding carboxylic acids. In general, the second oxidation step, from aldehyde to carboxylic acid, proceeds at a faster rate than the first step, i.e. the oxidation from alcohol to aldehyde. Under usual experimental conditions, the maximum fraction of aldehyde functions present will be between about 10 and 15% (based on the number of primary hydroxyls available for oxidation). The present process is especially favorable for the selective oxidation of primary hydroxyl groups in alcohols having a secondary alcohol function in addition to the primary alcohol, such as 1,6-octanediol, 1,9-octadecanediol, sugar alcohols, glycosides, and in particular carbohydrates having primary alcohol functions such as glucans (starch, cellulose), furanofructans, galactans, (galacto)mannans, and the like. A particular group of compounds suitable for oxidation wit the present process are hydroxyalkylated, especially hydroxyethylated carbohydrates such as hydroxyethyl starch or hydroxyethyl inulin. These derivatives result in an alternative way for producing formylmethyl and carboxymethyl carbohydrates.

The oxidation of carbohydrates containing primary hydroxyl groups results in the corresponding carbohydrates containing aldehydes and/or carboxylic acids with intact ring systems. Examples include α-1,4-glucan-6-aldehydes, β-2,1-fructan-6-aldehydes and β-2,6-fructan-1-aldehydes, with the corresponding carboxylic acids. Were these products still contain the aldehydes, they are useful intermediates for functional carbohydrates wherein the aldehyde groups are further reacted with e.g. amine compounds and the like. They are also useful intermediates for crosslinked carbohydrates, in which the aldehyde groups are further reacted with e.g. diamine reagents.

The process of the invention can be used for oxidizing and/or solubilizing carbohydrates and other high molecular weight primary alcohols such as proteinaccous materials, polyphenolic compounds, in residues to be removed from equipment used in food industry and in feed industry, and equipment used in water purification. Such equipment may especially be used in the production of dairy products, beer, wine and other beverages. Suitable examples of such equipment include pipes, tubes, capillaries, devices and, in particular, filters, including polymer membranes. Such cleaning procedures are preferably carried out by treating the equipment with an aqueous solution of the nitroxyl compound and the peracid, optionally in the presence of the halide. The concentration of the nitroxyl compound can advantageously be in the range of 1 to 100 mg per L, especially 3 to 30 mg/L, and the concentration of the peracid can be in the range of 0.5 to 10 mg per L. Bromide can be used, if desired, at a concentration between 1 and 200 mg/L. Further details on the nitroxyl-catalyzed treatment of filters and other equipment in the food industry can be found in WO 97/45523, which is incorporated herein by reference. WO 99/57159, incorporated herein by reference, gives ether details on the nitroxyl-catalyzed treatment of filters in water purification.

EXAMPLE 1

Oxidation of Methyl α-D-glucopyranoside (MGP)

One gram of MGP (5.15 mmol) was dissolved in 60 ml of water at room temperature To this solution were added 200 mg NaBr (1.94 mmol), 20 mg TEMPO (0.13 mmol), 10 mg EDTA (for stabilising the oxidising agent) and 2.5 g NaHCO$_3$. Peracetic acid (1.32 mmol/ml) was added at a rate of 200 µl per 10 minutes until an excess amount, calculated on a theoretical basis for 100% oxidation to 6-carboxylic acid (14.6 mmol), had been added. The pH was maintained at 7 by addition of 1 M NaOH using a pH-stat. The reaction time was 8 hr. The degree of oxidation, determined using the Blumenkrantz method with galacturonic acid as a reference, was 95%. High Performance Anion Exchange Chromatography (HPAEC) shows that the degree of oxidation is greater than 95%. No other peaks than the uronic acid and a trace of starting material were detected.

EXAMPLE 2

Oxidation of α-D-glucopyranosyl Phosphate (α-Glc-1-P)

1.97 g of α-Glc-1-P (2K$^+$.C$_6$H$_{11}$O$_9$P$^{2-}$.2H$_2$O, 5.5 mmol) was dissolved in 60 ml of water at room temperature. To this solution was added 210 mg KBr (1.76 mmol), 20 mg TEMPO (0.13 mmol), 10 mg EDTA, and 2.5 g KHCO$_3$. Peracetic acid (10 ml, 1.69 mmol/ml) was added at a rate of 200 µl per 10 minutes. The pH was maintained at 8 by addition of 2M KOH using a pH-stat. After 16 h the reaction was complete. The product crystallized from the mixture after addition of MeOH to obtain α-D-glucopyranuronic acid 1-phosphate (3K$^+$.C$_6$H$_8$O$_{10}$P$^{3-}$.5H$_2$O, 1.90 g, 4.0 mmol, 73%), NMR (500 Mhz, D$_2$O, in ppm): $^1$H δ 3,32 (dd, H-4J$_{3,4}$=9.5 Hz, J$_{4,5}$=9.9 Hz), 3.35 (m, H-2, J$_{P,H2}$=1.8 Hz, J$_{1,2}$=3.4 Hz, J$_{2,3}$=9.5 Hz), 3.62 (dd, H-3, J$_{2,3}$=9,5 Hz, J$_{3,4}$=9.5 Hz)), 3.99 (d, H-5, J$_{4,5}$=9.9 Hz,), 5.30 (dd, H-1, J$_{P,H1}$=7.3 Hz, J$_{1,2}$=3.4 Hz), $^{13}$C δ71.4 (C-2), 71.5 (C-3,C-4), 72.4 (C-5), 93.0 (C-1), 176.6 (C-6).

EXAMPLE 3

Oxidation of D-glucuronic Acid 1.94 g of D-glucuronic acid (10 mmol) was dissolved in 50 ml water at room temperature. To this solution was added 196 mg KBr (1.65 mmol), 30 mg TEMPO (0.20 mmol), 10 mg EDTA, and 1.0 g KHCO$_3$. Peracetic acid (8 ml, 1.69 mmol/ml) was added at a rate of 200 µl per 10 minutes. The pH was maintained at 8 by addition of 2M KOH using a pH-stat. After 16 h the reaction was complete. The reaction mixture was acidified with conc. HCl to pH=3.4 and the product was crystallized to obtain D-glucaric acid, monopotassium salt (K$^+$.C$_6$H$_9$O$_8$ g., 1.55 g, 0.62 mmol, 62%). FT-IR (in cm$^{-1}$): 3379 (s), 3261 (s), 2940 (m), 1738 (s), 1453 (m), 1407 (m), 1385 (m), 1342 (m), 1267 (m(, 1215 (m), 1108 (s), 1050 (m), 862 (m), 657 (m).

EXAMPLE 4

Oxidation of Starch at pH 5

One gram of potato starch (6.17 mmol) was gelatinized in 60 ml water at 100° C. To this solution were added 200 mg NsBr (1.94 mmol), 20 mg TEMPO (0.13 mmol), 10 mg EDTA and 2.5 g sodium acetate at room temperature. Peracetic acid (1.51 mmol/ml) was added at a rate of 200 µl per 10 minutes until an excess amount, calculated on a theoretical basis for 100% oxidation to 6-carboxylic acid (13.6 mmol) had been added. The pH was maintained at 5 with 1.0 M NaOH using a pH-stat. The reaction time was 8 hours. The degree of oxidation (Blumenkrantz—polygalacturonic acid) was 26% 6-carboxyl starch.

EXAMPLE 5

Oxidation of Starch at pH 6

One gram of potato starch (6.17 mmol) was gelatinized in 60 ml water at 100° C. To this solution were added 200 mg NaBr (1.94 mmol), 20 mg TEMPO (0.13 mmol), 10 mg EDTA, 1.25 g NaH$_2$PO$_4$ and 1.25 g Na$_2$HPO$_4$ at room temperature. Peracetic acid (1.30 mmol/ml) was added at a rate of 200 g per 10 minutes until an excess amount, calculated on a theoretical basis for 100% oxidation to 6-carboxylic acid (13.8 mmol), had been added. The pH was maintained at 6 with 1.0 M NaOH using a pH-stat. The reaction time was 8 hours. The degree of oxidation (Blumenkrantz—polygalacturonic acid) was 40% 6-carboxyl starch.

EXAMPLE 6

Oxidation of Starch at ph 7

One gram of potato starch (6.17 mmol) was gelatinized in 60 ml water at 100° C., To this solution were added 200 mg NaBr (1.94 mmol), 20 mg TEMPO (0.13 mmol), 10 mg EDTA and 2.5 g NaHCO$_3$, Peracetic acid (1.35 mmol/ml) was added at a rate of 200 µl per 10 minutes until an excess amount, calculated on a theoretical basis for 100% oxidation to 6-carboxylic acid (18.4 mmol), had been added. The pH was maintained at 7 with 1.0 M NaOH using a pH-stat. The reaction time was 11.5 hr. The degree of oxidation, determined using the Blumenkrantz method with polygalacturonic acid as a reference, was 95% 6-carboxyl starch. The degree of oxidation, determined with EPAEC was 86% 6-carboxyl starch.

EXAMPLE 7

Oxidation of Starch at pH 8

Example 4 was repeated, however maintaining the reaction pH at 8. The consumption of peracetic acid was 13.9 mmol. The degree of oxidation (Blumenkrantz—polygalacturonic acid) was 91% 6-carboxyl starch,

EXAMPLE 8

Oxidation of Starch at pH 9

Example 4 was repeated, however maintaining the reaction pH at 9. The consumption of peracetic acid was 11.9 mmol. The degree of oxidation (Blumenkrantz—polygalacturonic acid) was 90% 6-carboxyl starch.

EXAMPLE 9

Oxidation of Starch at pH 10

Example 4 was repeated (using 2.5 g of Na$_2$HPO4 instead of NaHCO$_3$). The consumption of peracetic acid (1.42 mmol/ml) was 14.3 mmol. The degree of oxidation was 37% 6-carboxyl starch.

What is claimed is:

1. A process for oxidizing a primary alcohol using an oxidizing agent in the presence of a catalytic amount of a di-tertiary-alkyl nitroxyl, comprising subjecting the primary alcohol to a peracid or a precursor thereof as the oxidizing agent and to said di-tertiary nitroxyl, in the presence of 0.1–40 mol % of halide, with respect to the primary alcohol.

2. A process according to claim 1, wherein the halide is bromide.

3. A process according to claim 1, wherein the di-tertiary-alkyl nitroxyl is 2,2,6,6-tetramethylpiperidin-1-oxyl (TEMPO).

4. A process according to claim 1, wherein a pH of 5–11 is used.

5. A process according to claim 4, wherein a pH of 7–10 is used.

6. A process according to claim 1, wherein the peracid is a peralkanoic acid.

7. A process according to claim 6, wherein the peracid is peracetic acid.

8. A process according to claim 1, wherein the peracid is produced in situ from hydrogen peroxide.

9. A process according to claim 1, wherein the primary alcohol is a carbohydrate.

10. A process according to claim 1, wherein the primary alcohol is a hydroxyalkylated carbohydrate.

11. A process according to claim 1, wherein the primary alcohol is present as a residual material on equipment used in the food industry.

12. A process according to claim 1, wherein the primary alcohol is present as a residual material on equipment used in water purification.

* * * * *